(12) United States Patent
Salas et al.

(10) Patent No.: US 7,258,856 B2
(45) Date of Patent: Aug. 21, 2007

(54) **PROTEASES FROM *CARICA* HAVING MITOGENIC ACTIVITY AND THEIR METHODS OF USE**

(76) Inventors: Carlos E. Salas, Rua Liguria 448, Bairro Bandeirantes, Bello Horizonte (BR) 31340-360; Miriam T. P. Lopes, Rua Liguria 448, Bairro Bandeirantes, Bello Horizonte (BR) 31340-360; Abraham V. Schnidermann, Arutro Pratt 105, Coquimbo (CL)

( * ) Notice: Subject to any disclaimer, the term of this patent is extended or adjusted under 35 U.S.C. 154(b) by 0 days.

(21) Appl. No.: 11/378,196

(22) Filed: Mar. 17, 2006

(65) Prior Publication Data

US 2006/0153830 A1    Jul. 13, 2006

Related U.S. Application Data

(63) Continuation-in-part of application No. 10/162,267, filed on Jun. 3, 2002, now abandoned.

(51) Int. Cl.
*A61K 38/46* (2006.01)
*A61K 38/48* (2006.01)
*A61K 38/00* (2006.01)
*C12N 9/50* (2006.01)
*C12N 9/48* (2006.01)

(52) U.S. Cl. .............. 424/94.65; 424/94.63; 514/12; 435/219; 435/212

(58) Field of Classification Search .......... 514/12; 424/94.65, 94.63; 435/219, 212
See application file for complete search history.

(56) References Cited

OTHER PUBLICATIONS

Abstract: "Protective effects of *Carica papaya* Linn on the exogenous gastric ulcer in rats", by CF Chen, SM Chen, SY Chow, and PW Han, *Am J. Chin Med*, vol. 9, No. 3, pp. 205-212 (Autumn 1981).

"Spontaneous processing of peptides during coagulation of latex from *Carica papaya*" by V. Moutim, L.G. Silva, M.T.P. Lopes, G. Wilson Fernandes and C.E. Salas, *Plant Science*, vol. 142, pp. 115-121 (1999).

"Changes in protein profile druing coagulation of latex from *Carica papaya*" by L.G. Silva, O. Garcia, M.T.P. Lopes and C.E. Salas, *Brazilian Journal of Medical and Biological Research*, Nov. 30, pp. 615-619 (1997).

"Bromelain, from Pineapple Stems, Proteolytically Blocks Activation of Extracellular Regulated Kinase-2 in T Cells" by Tracey L. Mynott, Andrew Ladhams, Pierre Scarmato, and Christian R. Engwerda, *The Journal of Immunology*, vol. 163, pp. 2568-2575 (1999).

"Caracterizacoes Bioquimica e Farmacologica Parciais, de Produto(s) Natural(ais) Derivado(s) de *Caricadeae*, com Atividade Mitogenica" by M.T.P. Lopes and C.E. Salas, *Ms Sc Dissertation, Federal University of Minas Gerais, Brasil* (1999) No English translation available.

"Isolation and Preliminary Characterization of the Cysteine-Proteinases from the Latex of *Carica candamarcensis* Hook" by Walreavens, et al., *Biol. Chem. Hoppe-Seyler*, vol. 374, pp. 501-506 (Jul. 1993).

"Crab collagenase in wound debridement" by Glyantsev, et al., *Journal of Wound Care*, vol. 6, No. 1, pp. 13-16 (Jan. 1997).

*Primary Examiner*—Maryam Monshipouri
(74) *Attorney, Agent, or Firm*—David G. Rossenbaum; J. Peter Paredes; Rosenbaum & Associates, PC

(57) ABSTRACT

Proteases having mitogenic activity isolated from the genus *Carica* are provided. In particular the proteases are cysteine proteases isolated from *Carica candamarcensis*. In addition, the recombinant forms of the protease, including fragments and mutants with substantial homology are provided. Also provided are pharmaceutical compositions useful for treating wounds that include the disclosed proteases with mitogenic activity. A method of treating wounds is provided using the disclosed proteases.

5 Claims, No Drawings

PROTEASES FROM *CARICA* HAVING MITOGENIC ACTIVITY AND THEIR METHODS OF USE

REFERENCE TO CROSS RELATED APPLICATIONS

The present application is a continuation-in-part of application Ser. No. 10/162,267, filed Jun. $3^{rd}$, 2002, now abondaned the disclosure of which are incorporated herein by reference.

FIELD OF INVENTION

The present invention relates to a group of proteolytic enzymes or proteases isolated from the genus *Carica*. In particular, the proteolytic enzymes are cysteine proteases that function as mitogenic stimulators of mammalian cells. The present invention also relates to a process for the production of these enzymes and their use as a wound healing promoter.

BACKGROUND

The skin is an important organ for homeostasis and host defense against foreign invaders. Specifically, it acts as the body's first line of defense against infection. Accordingly, it is important that lesions or wounds in the skin be rapidly closed to prevent infection. Some types of wounds, however, are resistant to healing under normal physiological conditions.

The process of wound healing involves a complex system of local and remote (systemic) resources. For example, amino acids and sugars are needed as substrates for collagen and proteoglycan synthesis. Migration of fibroblasts and epithelial/endothelial cells during the wound healing process places additional systemic demands on a subject during the wound healing process. Wounded tissues have unique nutritional needs and physiological features. Lymphocyte participation in wound healing has been demonstrated. Alteration in the hosts T-cell dependent immune response has also been shown to influence wound healing. Cyclosporine and anti T-cell antibodies, both of which interfere with T-cell function, abrogate wound healing. Similarly, macrophages and their products are also involved in wound healing. Increased circulation usually results in rapid delivery of monocytes and PMN's to the wound site. This in turn results in the elimination of bacterial contamination of the wound due to nonspecific killing mechanisms and also enhances the rate of wound healing. These various cell types are synthesized by the bone marrow.

While wound healing is typically an efficient and natural process that normally requires no special treatment, chronic non-healing wounds can occur. In the chronic cases, there is some underlying factor preventing healing and intervention is often necessary to complete the healing process. For example, pressure sores are initially acute wounds caused by ischaemic death of tissue due to excessive pressure and will usually heal readily when pressure is relieved and the blood supply restored. Often times it is difficult to resolve these causative factors and chronic wounds can develop. Most of these chronic wounds are characterized by the accumulation of devitalized tissue and cellular exudates at the outer surface. These products result from a restriction of nutrients to the damaged epithelium and form either a dry, hard eschar or, as in the case of deep moist wounds, a slough that frequently hardens on the outside with exposure to the air. The accumulation of these products in the wound bed is generally regarded to prevent or delay granulation and epithelialisation. The removal of this tissue by a process termed debridement is therefore thought to facilitate healing.

Debridement can be accomplished by both mechanical and non-mechanical methods. The mechanical methods require the physical elimination of the devitalized tissue from the healthy, but this difficult and often results in the aggravation of the wound. There are various non-mechanical debridement methods that include enzymes, hydrogels and chemical formulations. While various methods of debridement exist, there is no proven reliability of any particular method of debridement with respect to a particular wound. In particular, use of proteolytic enzymes in the early debridement (digestion and separation) of eschar tissues, such as in burn wounds, decubitus ulcers, pressure necroses and bed sores has been researched, e.g., streptokinase, trypsin and papain.

There remains a need for isolating and providing an agent that acts as an effective promoter of wound healing.

SUMMARY OF INVENTION

Aspects of the present invention satisfy the unmet needs in the art, as disclosed above. In particular, the invention provides a natural protease isolated from *Carica*, or its metabolites, along with recombinant forms of the natural protease, including fragments and mutants, that exhibit protease activity comparable to the wild type protease.

Another aspect of the present invention provides a pharmaceutical composition comprising an amount of protease effect for wound treating, wherein the protease comprises one of the proteins disclosed herein, which includes the natural, recombinant, fragment, and mutant forms of the protease.

In another aspect of the present invention, a method of treating wounds is provided using the compositions disclosed herein. The compositions containing the proteins of the present invention are used for treating various wounds, including chronic wounds like ulcers.

Still another aspect of the present invention provides a protease having mitogenic or proliferative activity. The protease is preferably a cysteine protease and more preferably a protease isolated from *Carica*, particularly *Carica candarmacensis*.

These and other aspects of the invention will be obvious to those of ordinary skill in the art considering the provided disclosure and examples.

DETAILED DESCRIPTION OF PREFERRED EMBODIMENTS

The present invention relates to proteases, more particularly, cysteine proteases, and the production and use thereof. In particular, the one aspect of the present invention relates to a group of cysteine proteases, termed CC23a–e. This group of cysteine proteases is characterized as immunologically distinct from papain, having a molecular mass of about 23,000 Da and having a distinct net charge.

In another aspect of the present invention, a process for the production of the disclosed cysteine proteases is provided comprising separation of the protease from latex or leaf plant material of Caricaceae and purification therefrom, including *Carica candarmacensis* and *Carica papaya*.

The disclosed cysteine proteases can be used to enhance the process of debridement and wound healing of eschar tissue resulting from burn wounds, sores and ulcers, for example. Another aspect of the present invention comprises an enzyme preparation specifically adapted for use in enhancing the process of debridement and wound healing. Another aspect of the present invention provides a pharmaceutical composition which comprises at least one of the present cysteine proteases CC23a–e and at least one pharmaceutically-acceptable carrier.

As indicated above, the cysteine proteases CC23a–e have a relative molecular mass of 23,000 Da and are highly basic proteins, having a pI greater than 9.5, and exhibit faster migration in a cathodal electrophoresis system. CC23a–e require thiol compounds for full activity and is inhibited by the class-specific inhibitors E-64 [L-3-carboxy-2,3-trans-epoxypropionyl-leucylamido (4-guanidino) butane] and chicken cystatin.

These cysteine proteases may be obtained by conventional preparative fast protein liquid chromatography (FPLC) cation-exchange chromatography at pH 9.2. Currently, commercially available crude latex extract powders (Technologic Farm) are commonly used as a source of the present proteases. More specifically, an extract may be chromatographed using a cation exchanger (Mono S) using a Pharmacia FPLC system and a gradient of 0.005 M to 1.0 M sodium chloride at pH 9.0. A variety of substrates may be used to assay the fractions for cysteine protease activity. The different proteases can be identified on the basis of their different substrate specificities.

The proteases can also be produced using recombinant DNA techniques. The sequence of a cysteine protease, e.g., CC23a, is determined using known protein sequencing techniques, including Edman degradation. Based on the determined amino acid sequence, DNA primers are synthesized. These DNA primers can be used in RT-PCR reactions to select the cDNA which code for this particular cysteine protease. Once the identity is confirmed, the recombinant cDNA can be cloned into an appropriate expression vector using well-known cloning techniques. The resulting expression vector can be used to transform an appropriate cell line to express the recombinant cysteine protease, which can be isolated using standard purification techniques. The proliferative property of the recombinant cysteine protease can be tested as done with the naturally derived protease.

Preferred mutants or fragments of the cysteine proteases disclosed herein have corresponding amino acid sequences, in relation to the natural amino acid sequence, that are substantially homologous. Substantially homology is used to describe amino acid sequences that have near identity to the naturally occurring protease but contain substitutions that do not greatly alter function. Specifically, substantially homologous means a protein having a sequence that has at least about 80%, usually at least about 90% and more usually at least about 98% sequence identity with the sequence of the disclosed cysteine protease, as measured by BLAST.

Site-directed mutagenesis can be used to create mutations of the proteases that still retain proliferative activity. Preferably, conservative mutations are contemplated. The conservative substitutions can be introduced by modification of DNA encoding for the polypeptides of the invention. A conservative substitution is recognized in the art as a substitution of one amino acid for another amino acid that has similar properties, typically allowing the expression of a functional protein.

The present cysteine proteases may be admixed with pharmaceutically-acceptable carriers for application to patients. The generally preferred route of administration is by topical application to the site of a wound or ulcer. The pharmaceutical preparation may be in the form of a sterile solution that is applied to an inert dressing, such as a gauze pad, a gel, or ointment that is placed directly on the wound.

Such pharmaceutical compositions may contain the cysteine protease(s) in an active form, or, preferably, in an inactive form in which the active site cysteine residue forms half of a disulphide bridge. The other half comprises a pharmaceutically-acceptable thiol compound, for example the amino acid cysteine. The present formulations may be prepared immediately before use by mixing a lyophilised preparation of the cysteine protease with an aqueous solution. If an enzyme is present in an inactive form, an activating agent, for example cysteine, must be added to regenerate the free active site thiol of the protease.

The cysteine proteases described herein are proliferative factors useful for enhancing the healing of wounds. An amount of the protease effective for wound healing is readily determined by one of ordinary skill in the art using standard techniques, and such an amount is applied to the wound by standard techniques known in the art. Preferably, the amount of protease effective for wound healing is a concentration ranging from about 50 ng/ml to about 500 ng/ml as a single application, or in dosing regimens that range from several times per day to once every few days for a period of one to several weeks. In a topical formulation, the amount effective for wound healing is about 0.01 µg/cm$^2$ to about 100 µg/cm$^2$ of cysteine protease administered directly to the wound. These cysteine proteases can be used to treat many types of chronic non-healing wounds, such as fall-thickness dermal ulcers, e.g., pressure sores, venous ulcers, and diabetic ulcers; to treat acute wounds such as burns, incisions, and injuries; and to speed the healing of wounds associated with reconstructive procedures such as skin grafting and flap placement, e.g., in the repairing of wounds and aiding cosmetic procedures. In addition, the cysteine proteases can be used to treat damage to the gastric epithelium, the lung epithelium, and other internal epithelial layers.

In cases where the cysteine proteases of this invention are being used for surface wound healing, they can be administered by topical means. For topical administration, the cysteine proteases are applied directly to the site of injury as a solution, spray, gel, cream, ointment or as a dry powder. Slow release devices directing these cysteine proteases to the injured site can be used. In addition, the cysteine proteases can be combined with topical bandages, or dressings, or sutures/staples, and with topical creams and ointments. In specific, the cysteine proteases of this invention can be used at a concentration ranging from about 50 ng/ml to about 500 ng/ml as a single application, or in dosing regimens that range from several times per day to once every few days for a period of one to several weeks. Usually, the amount of topical formulation administered is an amount which applies about 0.01 µg/cm$^2$ to about 100 µg/cm$^2$ of cysteine protease to the wound.

Cysteine proteases of this invention can also be used for in vitro culturing of responsive cell types, e.g., fibroblasts or epithelial cells. For such uses, the cysteine proteases can be added to the cell culture medium at a concentration of about 10 ng/ml to about 100 ng/ml. In addition, cells grown under growth factor stimulation can be used as a source of expanded cell populations for grafting purposes. For all of these applications, the cysteine proteases of this invention may be used alone or in combination with other proliferative factors, debriding agents and biologically active agents. Other debriding agents include trypsin, collagenase dextranomer, cadexomer iodine, and hydrogels, e.g., INTRASITE GEL®. (Smith & Nephew Healthcare Ltd), STERIGEL®. (Seton Healthcare Group plc) and GRANUGEL®. (CovaTec UK, Ltd.).

EXAMPLE 1

Purification of CC23a–e from Latex Extract of *Carica candarmacensis*

Crude latex extract from *Carica* candarmacensis was dissolved in 1 M sodium acetate buffer, 1 mM EDTA, 0.01% sodium azide, pH 5.0. This was filtered through 0.22 □m filters and the protein content was determined by absorption at 280 nm using an $A_{1\%,280}$ of 20.1(Murachi, T. and Yasui, M., Biochemistry, 4, 2275–2282, 1965). The preparation was then chromatographed on a G-10 filtration column (Amersham-Pharmacia) and eluted with the same buffer. The first peak corresponded to the bulk protease activity and was pooled and applied onto a CM-Sephadex column (Amersham-Pharmacia). The protein fractions were eluted with a linear gradient of 0.05 M to 1.0 M sodium acetate, pH 5.0 (essentially as described previously for chymopapain in Buttle, D. J., and Barrett, A. J., *Biochem. J.*, 223, 81–88, (1984)). The second protein peak containing the protease activity termed CC23a–e was pooled and applied onto a Mono S HR 10/10 column of a FPLC system (Pharmacia). The protein mix was eluted with a gradient of 0.002 M to 1.0 M NaCl at pH 9.2.

Plots of $A_{280}$ and gradient composition were provided automatically. The fractions were stored, tightly capped at 4° C. until assayed and further processed. The five peaks eluting between 0.02 M and 0.39 M NaCl were taken and designated as peaks CC23a–e. Each of the peaks CC23a–e were concentrated and dialyzed in an Amicon PM10 concentration chamber against 10 mM sodium acetate, 1 mM EDTA, 0.01% sodium azide, pH 6.5 at 4° C.

EXAMPLE 2

Proliferation Assays

The above purified proteins, CC23a–e, their metabolites, or the crude extracts from which were derived, were assayed for their proliferative activity as follows. The mitogenic fractions were assayed as described below, using either fibroblasts (i.e., L929), epithelial cells (i.e., human keratinocytes), or human mammary cells (i.e., MDA MB 231). Fractions (5–50 ng/ml) were tested for proliferative activity by measuring the effect of aliquots of the fractions on DNA synthesis. This was accomplished by actually measuring the proliferation of L929, MDA MB 231 and keratinocytes cells by monitoring the incorporation of [$^3$H]-thymidine into DNA and/or by measuring the increase in cell number, using MTT as an indicator.

Cells were plated at $1-2\times10^4$ cells/well (Costar, Cambridge, Mass.) in RPMI 1640 (GIBCO, Grand Island, N.Y.) supplemented with 10% fetal calf serum (GIBCO, Grand Island, N.Y.) and antibiotics (100 units/ml penicillin and 100 µg/ml streptomycin sulfate, GIBCO, Grand Island, N.Y.). After 24–48 h at 37° C., 2, 5% $CO_2$, cells were washed twice with phosphate-buffered saline, and the medium was replaced with 0.5% FBS RPMI 1640 supplemented with antibiotics for 24–36 h before the assay.

Test samples were then added at the specified concentrations during 24 to 72 h. One µCi [$^3$H]-thymidine/well (Amersham Pharmacia) was added and remained in the assay for 18 h before arresting the reaction. The reaction was stopped by 2 washes with RPMI, 2 washes with 5% TCA and 2 washes with 95% ethanol. The remaining radioactivity was measured following treatment with Aquasol (Amersham-Phamacia) in a scintillation counter. The following table, Table 1, summarizes the proliferative effect of CC23a–e fractions on L929 cells.

TABLE 1

| Protein tested | 10 ng/mL | 20 ng/mL | 50 ng/mL |
| --- | --- | --- | --- |
| Crude Fraction | 105% | 17% | 31% |
| CC23a (SEQ ID NO: 1) | 69% | 61% | 98% |
| CC23b | 54% | 93% | 67% |
| CC23c | 18% | 11% | 16% |
| CC23d | 8% | — | 18% |
| CC23e | 61% | 36% | 32% |
| Papain | — | 25% | — |

The determined proliferative activity (assayed as [$^3$H]-thymidine incorporation into L929 cells) showed that the purified form of CC23a–e was not destroyed by heating to 90° C. for 5 minutes but was significantly destroyed (60%) by exposure to the cysteine protease inhibitor E64 for a period of 30 min (data not shown).

As shown in Table 1, the purified protein CC23a stimulated close to 100% proliferation of L929 fibroblast cells at a concentration of 50 ng/ml, while the maximal stimulatory effect of CC23d was 18% at 50 ng/ml. Papain from Sigma, but not chymopapain, showed 25% stimulatory affect at 20 ng/ml using the same protocol. The proliferative effect of each protease tested was also reduced by the addition of the inhibitor E64.

EXAMPLE 3

N-Terminal Sequencing

The amino acid sequence of the purified form of the protease CC23a, CC23b, and CC23c was determined. Approximately 1.7 µg of protein, obtained after cation exchange-MonoS chromatography, was loaded onto an Applied Biosystems gas-phase protein sequencer. Two hundred and fourteen rounds or fifteen rounds of Edman degradation were carried out, and identification of amino acid derivatives were made with an automated on-line PTH-amino acid analyzer (model 477A, Applied Biosystems, Foster City, Calif.).

The two hundred and fourteen rounds of Edman degradation of CC23a resulted in the identification of the 214 amino acid residues, depicted as SEQ ID NO:1 (YPESIDWRQKGAVTPVKDQNPCGSCWAFST-VATVEGINKIVTGKLISLSEQELLDCDRR SHGCKG-GYQTTSLQYVVDNGVHTEKVYPYEKKQGKCRAKD KQGPWVKITGYKRVPS NDEISLIKAIATQPVSV-LVESKGRAFQFYKGGVFGGPCGT-KLDHAVTAVGYGKDYILIKN SWGLRWGDKGYIKIK-NASGNSEGICGVYKSSYFPIKGYQ).

The fifteen rounds of Edman degradation of CC23b and CC23c resulted in the identification of the first 15 N-terminal amino acid residues, depicted as SEQ ID NO:2 (YPGS-VDWRQK GAVTP).

EXAMPLE 4

Treatment of Wound of Patient

A patient diagnosed with a non-healing wound, specifically a lesion on the skin unable to heal without intervention, is selected for treatment with the cysteine protease CC23a. The purified protease CC23a can be used at a concentration of about 200 ng/ml as a single application, twice daily for a period of about a week. The amount of topical formulation administered to a patient is an amount which applies about 25 µg/cm$^2$ of CC23a to the lesion.

After treatment for approximately a week, the non-healing lesion shows signs of undergoing healing.

What is claimed is:

1. A composition comprising a substantially purified protein having an amino acid sequence of SEQ ID NO:1, wherein the composition further comprises a pharmaceutically acceptable carrier.

2. The composition of claim 1, wherein the substantially purified protein is found in plants of the family Caricaceae.

3. The composition of claim 2, wherein the substantially purified protein is found in *Carica candamarcensis*.

4. The composition of claim 1, further comprising at least one antibiotic.

5. The composition of claim 1, further comprising at least one protein denaturing agent.

* * * * *

SEQUENCE LISTING

<160> NUMBER OF SEQ ID NOS: 2

<210> SEQ ID NO 1
<211> LENGTH: 214
<212> TYPE: PRT
<213> ORGANISM: Carica candamarcensis

<400> SEQUENCE: 1

```
Tyr Pro Glu Ser Ile Asp Trp Arg Gln Lys Gly Ala Val Thr Pro Val
1               5                   10                  15

Lys Asp Gln Asn Pro Cys Gly Ser Cys Trp Ala Phe Ser Thr Val Ala
            20                  25                  30

Thr Val Glu Gly Ile Asn Lys Ile Val Thr Gly Lys Leu Ile Ser Leu
        35                  40                  45

Ser Glu Gln Glu Leu Leu Asp Cys Asp Arg Arg Ser His Gly Cys Lys
    50                  55                  60

Gly Gly Tyr Gln Thr Thr Ser Leu Gln Tyr Val Val Asp Asn Gly Val
65                  70                  75                  80

His Thr Glu Lys Val Tyr Pro Tyr Glu Lys Gln Gly Lys Cys Arg
                85                  90                  95

Ala Lys Asp Lys Gln Gly Pro Trp Val Lys Ile Thr Gly Tyr Lys Arg
            100                 105                 110

Val Pro Ser Asn Asp Glu Ile Ser Leu Ile Lys Ala Ile Ala Thr Gln
            115                 120                 125

Pro Val Ser Val Leu Val Glu Ser Lys Gly Arg Ala Phe Gln Phe Tyr
    130                 135                 140

Lys Gly Val Phe Gly Gly Pro Cys Gly Thr Lys Leu Asp His Ala
145                 150                 155                 160

Val Thr Ala Val Gly Tyr Gly Lys Asp Tyr Ile Leu Ile Lys Asn Ser
                165                 170                 175

Trp Gly Leu Arg Trp Gly Asp Lys Gly Tyr Ile Lys Ile Lys Asn Ala
            180                 185                 190

Ser Gly Asn Ser Glu Gly Ile Cys Gly Val Tyr Lys Ser Ser Tyr Phe
            195                 200                 205

Pro Ile Lys Gly Tyr Gln
    210
```

<210> SEQ ID NO 2
<211> LENGTH: 15
<212> TYPE: PRT
<213> ORGANISM: Carica candamarcensis

<400> SEQUENCE: 2

```
Tyr Pro Gly Ser Val Asp Trp Arg Glx Lys Gly Ala Val Thr Pro
1               5                   10                  15
```